US006214882B1

(12) United States Patent
Purcell et al.

(10) Patent No.: US 6,214,882 B1
(45) Date of Patent: *Apr. 10, 2001

(54) BENZENESULPHONAMIDE DERIVATIVES, PREPARATION THEREOF AND THERAPEUTICAL USES THEREOF

(75) Inventors: Thomas Purcell, Montfort l'Amaury; Christophe Philippo, Rueil Malmaison, both of (FR)

(73) Assignee: Synthelabo, Le Plessis Robinson (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/000,336

(22) PCT Filed: Aug. 1, 1996

(86) PCT No.: PCT/FR96/01215

§ 371 Date: Jan. 16, 1998

§ 102(e) Date: Jan. 16, 1998

(87) PCT Pub. No.: WO97/06136

PCT Pub. Date: Feb. 20, 1997

(30) Foreign Application Priority Data

Aug. 4, 1995 (FR) .................................... 95 09503

(51) Int. Cl.⁷ ........................ A01N 41/06; C07C 303/00
(52) U.S. Cl. ........................ 514/602; 514/600; 514/601; 514/604; 564/85; 564/86; 564/88
(58) Field of Search ..................... 514/600, 601, 514/602, 604; 564/86, 88, 85

(56) References Cited

U.S. PATENT DOCUMENTS 3,860,647 * 1/1975 Colella et al. .
3,943,254 * 3/1976 Colella et al. .
4,140,713 * 2/1979 Oxford et al. .
4,217,305 * 8/1980 Imai et al. .
4,711,899   12/1987 Gaudilliere et al. .
4,724,148 * 2/1988 Sonobe et al. .
4,765,988 * 8/1988 Sonobe et al. .
5,405,872 * 4/1995 McDermed et al. .
5,663,205 * 9/1997 Ogawa et al. .

FOREIGN PATENT DOCUMENTS 0 034 432   8/1981 (EP) .
0 538 469   4/1993 (EP) .

OTHER PUBLICATIONS

Fujikura et al, "Studies on benzenesulphonamid derivatives with alpha– and beta–adrenergic antagonistic and antihypertensive activites", Chemical and Pharmaceutical Bulletin, vol. 30, No. 11, Nov. 1982, pp. 4092–4101.

* cited by examiner

*Primary Examiner*—James O. Wilson
(74) *Attorney, Agent, or Firm*—Jacobson, Price, Holman & Stern, PLLC

(57) ABSTRACT

Benzenesulphonamide compounds of general formula (I), wherein $R_1$ is a hydrogen or halogen atom such as chlorine or fluorine, or a straight or branched $C_{1-4}$ alkyl or $C_{1-4}$ alkoxy group, each of $R_2$, $R_3$ and $R_4$, which are the same or different, is a hydrogen atom or a straight, branched or cyclic $C_{1-4}$ alkyl group, and $R_1$ is a hydrogen atom or a $C_{1-2}$ alkyl, $C_{1-2}$ fluoroalkyl or $C_{1-2}$ perfluoroalkyl group, in the form of enantiomers, diastereoisomers or mixtures thereof, including racemic mixtures, as well as pharmaceutically acceptable acid addition salts thereof, are provided for therapeutical use.

15 Claims, No Drawings

BENZENESULPHONAMIDE DERIVATIVES, PREPARATION THEREOF AND THERAPEUTICAL USES THEREOF

The present invention relates to benzenesulphonamide derivatives, to their preparation and to their application in therapy.

The compounds of the invention correspond to the general formula (I)

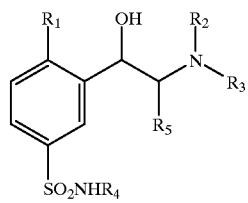

in which:
$R_1$ represents a hydrogen atom, a halogen atom such as chlorine or fluorine or a linear or branched $C_{1-4}$ alkyl or $C_{1-4}$ alkoxy group,
$R_2$, $R_3$ and $R_4$ represent, independently of one another, hydrogen atoms or linear, branched or cyclic $C_{1-4}$ alkyl groups, and
$R_5$ represents a hydrogen atom or a $C_{1-2}$ alkyl, $C_{1-2}$ fluoroalkyl or $C_{1-2}$ perfluoroalkyl group.

The term $C_{1-4}$ alkyl comprises linear, branched-chain or cyclized radicals having up to 4 carbon atoms, comprising methyl, ethyl, propyl, isopropyl, butyl, isobutyl and tert-butyl, preferably $C_{1-2}$ alkyl such as methyl and ethyl.

The term $C_{1-2}$ fluoroalkyl comprises linear radicals having 1 to 2 carbon atoms as defined above, in which at least one of the hydrogen atoms is substituted with a fluorine, on the understanding that not all the hydrogen atoms are substituted with fluorine atoms. The term $C_{1-2}$ perfluoroalkyl comprises linear radicals having 1 to 2 carbon atoms as defined above, in which all the hydrogen atoms are substituted with a fluorine.

The term $C_{1-4}$ alkoxy comprises linear radicals having up to 4 carbon atoms, attached via an oxygen atom, comprising methoxy, ethoxy, propoxy, isopropoxy, butoxy, isobutoxy and tert-butoxy, preferably $C_{1-2}$ alkoxy, methoxy and ethoxy.

The compounds of general formula (I) contain one or more asymmetric carbon atoms. They may hence exist in the form of enantiomers or diastereoisomers. These enantiomers and diastereoisomers as well as mixtures thereof, including the racemic mixtures, form part of the invention.

The compounds of general formula (I) can take the form of addition salts with pharmaceutically acceptable acids, which also form part of the invention. According to the present invention, the preferred salts are the oxalate and fumarate salts.

The compounds of general formula (I) in which $R_5$ represents a $C_{1-2}$ alkyl, $C_{1-2}$ fluoroalkyl or $C_{1-2}$ perfluoroalkyl group exist in the form of syn or anti isomers. These forms as well as mixtures thereof form part of the invention.

Preferred compounds are those for which $R_5$ represents a hydrogen atom, a methyl or an ethyl, preferably a hydrogen or a methyl, in the form of enantiomers or diastereoisomers or mixtures of these different forms, including racemic mixtures, as well as their addition salts with pharmaceutically acceptable acids.

Other preferred compounds are those for which $R_1$ represents a hydrogen atom, a fluorine, a chlorine or a $C_{1-4}$ alkoxy group, preferably methoxy or ethoxy, in the form of enantiomers or diastereoisomers or mixtures of these different forms, including racemic mixtures, as well as their addition salts with pharmaceutically acceptable acids.

Other compounds of choice are those for which $R_2$ and $R_3$ represent, independently of one another, a hydrogen atom, a methyl, an ethyl or an isopropyl, preferably a hydrogen, in the form of enantiomers or diastereoisomers or mixtures of these different forms, including racemic mixtures, as well as their addition salts with pharmaceutically acceptable acids.

Among these, there may be mentioned the compounds for which:
$R_1$ represents a hydrogen atom, a fluorine, a chlorine or a $C_{1-4}$ alkoxy group, preferably methoxy or ethoxy,
$R_2$ and $R_3$ represent, independently of one another, a hydrogen atom, a methyl, an ethyl or an isopropyl, preferably a hydrogen,
$R_4$ represents a hydrogen or a linear, branched or cyclic $C_{14}$ alkyl group, and
$R_5$ represents a hydrogen atom, a methyl or an ethyl, preferably a hydrogen atom or a methyl, in the form of enantiomers or diastereoisomers or mixtures of these different forms, including racemic mixtures, as well as their addition salts with pharmaceutically acceptable acids, and very special mention may be made of
α-(aminomethyl)-2-methoxy-5-sulphamoylbenzenemethanol and its salts,
(+)-α-(aminomethyl)-2-methoxy-5-sulphamoylbenzenemethanol and its salts,
(−)-α-(aminomethyl)-2-methoxy-5-sulphamoylbenzenemethanol and its salts,
α-(aminomethyl)-2-chloro-5-sulphamoylbenzenemethanol and its salts, and
α-(aminomethyl)-2-fluoro-5-sulphamoylbenzenemethanol and its salts.

The compounds of general formula (I) in which $R_1$ represents an alkoxy group and $R_2$ and $R_3$ represent hydrogen atoms may be prepared according to the process shown in Appendix 1, which consists in treating a benzaldehyde derivative of formula (V), in which $R_1$ is defined as above, with ethyl orthoformate in the presence of ammonium chloride, and then with chlorosulphonic acid, in treating the 5-chlorosulphonylbenzaldehyde derivative of formula (IV) with an amine of formula $R_4NH_2$ in which $R_4$ is defined as in the general formula (I), in thereafter reacting the 5-sulphamoylbenzaldehyde derivative of formula (III) with trimethylsilyl cyanide (TMSCN) in the presence of zinc iodide, and lastly reducing the compound of formula (II) thereby obtained with lithium borohydride in the presence of trimethylsilyl chloride (TMSCl).

The compounds of general formula (I) may also be prepared according to the process shown in Appendix 2, from a sulphamoylacetophenone derivative of formula (XII).

In the case where $R_1$ is defined as in the general formula (I) with the exception of the meaning alkyl, this process consists in treating the 5-sulphamoylphenyl ketone derivative of formula (XII) with bromine, in then reacting the compound of formula (XI), either with lithium chloride to obtain the compound of formula (X) which is thereafter reduced with borane to give the compound of formula (IX) and then treated with sodium azide to give the compound of formula (VIII), or with sodium azide and then sodium borohydride to obtain the compound of formula (VIII), or with sodium borohydride in the presence of potassium carbonate to obtain the compound of formula (VII), and lastly in treating the compound of formula (VIII) with hydrogen in the presence of a catalyst such as palladium on charcoal in the case where $R_1$ is not a chlorine atom, or with triphenylphosphine and then with aqueous ammonia in the case where $R_1$ is a chlorine atom, to obtain the compound of general formula (I) in which $R_2$ and $R_3$ are hydrogen atoms, or in treating the compound of formula (VII), either with an amine of formula $R_2(R_3)NH$ in which $R_2$ represents a hydrogen atom or a $C_{1-4}$ alkyl group and $R_3$ a $C_{1-4}$ alkyl group, to obtain the compound of general formula (I) in which $R_2$ and $R_3$ are defined as above, or with an amine of formula $R_2(Bn)NH$ in which $R_2$ is a $C_{1-4}$ alkyl group and Bn a benzyl group, to obtain a compound of formula (VI), which is thereafter reduced with hydrogen in the presence of a catalyst such as palladium on charcoal, to give the compound of general formula (I) in which $R_2$ is an alkyl group.

In the case where $R_1$ is an alkyl group, this process consists in treating the compound of formula (XII) with benzyltrimethylammonium dichloroiodate to obtain the compound of formula (X) in which $R_1$ is an alkyl group, which is thereafter treated as described above to obtain the compound of general formula (I) in which $R_2$ and $R_3$ are hydrogen atoms and $R_1$ an alkyl group, via the corresponding intermediate compounds of formulae (IX) and (VIII).

The compounds of formula (XII)

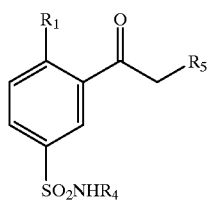

(XII)

in which $R_1$, $R_4$ and $R_5$ are defined as in the general formula (I), may be prepared by reacting a phenyl ketone derivative of formula (XIV)

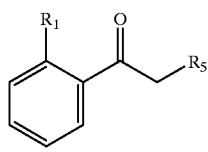

(XIV)

in which $R_1$ is defined as in the general formula (I), with chlorosulphonic acid, to give a chlorosulphonylphenyl ketone derivative of formula (XIII)

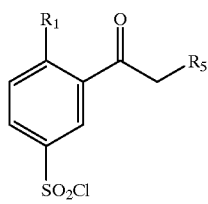

(XIII)

which is thereafter treated with an amine of formula $R_4NH_2$ in which $R_4$ is defined as in the general formula (I).

The compounds of formula (XII) in which $R_4$ represents a hydrogen atom may also be prepared by reacting a compound of formula (XVII)

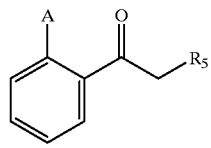

(XVII)

in which A is identical to $R_1$ as defined in the general formula (I) or alternatively represents a hydroxyl group, with nitric acid, to obtain a nitrophenyl ketone derivative of formula (XVI)

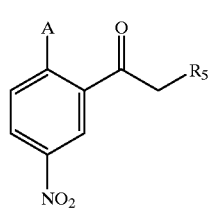

(XVI)

which is reduced to an aminophenyl ketone derivative with hydrogen in the presence of palladium on charcoal or with tin chloride, where appropriate after treatment with an alkyl iodide in the case where A represents a hydroxyl group, to obtain the corresponding 2-alkoxyphenyl ketone derivative, and lastly treating the compound of formula (XV)

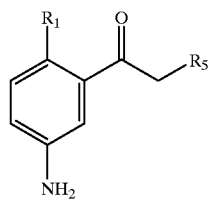

(XV)

with sodium nitrite, cuprous chloride and sulphur dioxide.

The enantiomers of the compounds of general formula (I) are prepared from the enantiomers of the compounds of formula (VIII)

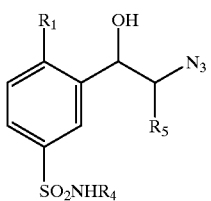

(VIII)

which are themselves obtained, either by enantioselective synthesis, which comprises treatment of the compound of formula (XI)

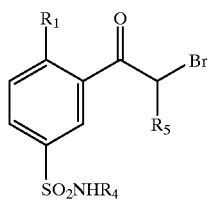

(XI)

with sodium azide and reaction of the compound of formula (XVIII) thereby obtained

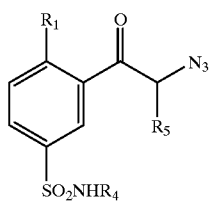

(XVIII)

with (+)- or (−)-B-chlorodiisopinocampheylborane (DIP-Cl) to obtain the (+) and (−) enantiomers, respectively, of the compound of formula (VIII), or by enzymatic resolution of the compound (IX)

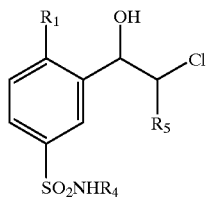

(IX)

which comprises treatment of the racemic compound of formula (IX) with acetic acid, selective enzymatic hydrolysis with the lipase SP 523 (lipase obtained by a recombinant DNA technique from *Aspergillus orysae*) of the compound of formula (XIX) thereby formed

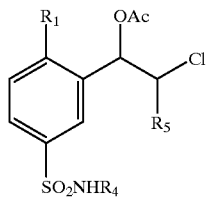

(XIX)

leading to the (+) enantiomer of the compound of formula (IX) and to the (−) enantiomer of the unhydrolysed compound of formula (XIX), separation by chromatography of the (+) enantiomer of the compound of formula (IX) and of the (−) enantiomer of the compound of formula (XIX) and hydrolysis of the (−) enantiomer of the compound of formula (XIX) to obtain the (−) enantiomer of the compound of formula (IX), and lastly reaction of the (+) and (−) enantiomers of the compound of formula (IX) with sodium azide, or by chemical resolution, which comprises reaction of the compound of formula (VIII) with N-carbobenzyloxy-L-alanine (N-CBZ-alanine), separation by chromatography and then hydrolysis of the enantiomers of the compound of formula (XX)

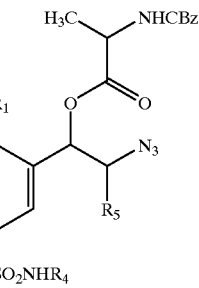

(XX)

The salts of the compounds of general formula (I) are obtained by reacting the compounds of general formula (I) in base form with pharmaceutically acceptable acids.

The starting materials are known in the literature or directly available on the market.

The examples which follow illustrate the processes and techniques which are suitable for the preparation of this invention, without, however, limiting the scope of the claim. The elemental microanalyses and the NMR and IR spectra confirm the structures of the compounds obtained.

EXAMPLE 1

α-(Aminomethyl)-2-methoxy-5-sulphamoylbenzenemethanol methanesulphonate 1.1. 2-Methoxy-5-sulphamoylbenzaldehyde This compound is obtained according to the process described in Patent FR 73/35277, by passing a stream of ammonia into a solution of 2-methoxy-5-chlorosulphonylbenzaldehyde in chloroform.

According to the same process, by treating 2-methoxy-5-chlorosulphonylbenzaldehyde with 10 equivalents of amine of formula $R_4NH_2$ for 3 hours at room temperature, the following compounds were obtained:

2-Methoxy-5-methylsulphamoylbenzaldehyde.
Melting point: 118° C.
2-Methoxy-5-cyclopropylsulphamoylbenzaldehyde.
Melting point: 162° C.
2-Methoxy-5-isopropylsulphamoylbenzaldehyde.
Melting point: 125° C.
2-Methoxy-5-t-butylsulphamoylbenzaldehyde.
Melting point: 99° C.

1.2. α-Aminomethyl-2-methoxy-5-sulphamoylbenzenemethanol 10.4 g (48.3 mmol) of 2-methoxy-5-sulphamoylbenzaldehyde and 18.4 ml (96.6 mmol) of trimethylsilyl cyanide are introduced into a 100-ml round-bottomed flask, 0.5 g (1.56 mmol) of zinc iodide is then added and the mixture is stirred at room temperature for 10 minutes. 20 ml of anhydrous tetrahydrofuran are then added and the solution is transferred into a dropping funnel.

Separately, 100 ml of anhydrous tetrahydrofuran and 2.6 g (119 mmol) of lithium borohydride are introduced into a 500-ml round-bottomed flask. The solution is stirred, 30 ml (236 mmol) of trimethylsilyl chloride are then added dropwise and the mixture is stirred at room temperature for 10 minutes.

The solution of trimethyl silyl cyanohydrin prepared above is then added dropwise. The mixture is stirred for 16 hours, 20 ml of ethanol are then added dropwise and the solution is concentrated. 120 ml of 20% potassium hydroxide solution are then added dropwise and the solution is concentrated. The residue is purified by column chromatography with a 90:9:1 mixture of dichloromethane, methanol and aqueous ammonia, then recrystallized in ethanol and dried in a desiccator under vacuum over phosphorus pentoxide. 0.30 g of product is obtained.
Melting point: 217–220° C.

1.3. α-Aminomethyl-2-methoxy-5-sulphamoylbenzenemethanol methanesulphonate

One equivalent of methanesulphonic acid in 2M solution in methanol is added to the product obtained in step 1.2. after recrystallization in methanol and diethyl ether and drying in a desiccator under vacuum over phosphorus pentoxide, 0.370 g of product is obtained.
Melting point: 210–212° C.

EXAMPLE 2

(−)-α-(Aminomethyl)-2-methoxy-5-sulphamoylbenzenemethanol methanesulphonate 2.1. 2-Methoxy-5-chlorosulphonylacetophenone 951 g (8.16 mol) of chlorosulphonic acid are introduced in a 1-liter round-bottomed flask. The mixture is cooled to about −5° C., and 81.5 g (0.544 mol) of 2-methoxyacetophenone are then added dropwise without exceeding 0° C. The mixture is then stirred at room temperature for 16 hours, and thereafter poured slowly onto crushed ice while stirring. The product is filtered off, washed with ice-cold water and then dried in a desiccator under vacuum over phosphorus pentoxide. 87.5 g of product are obtained.
Melting point: 85–86° C.

2.2. 2-Methoxy-5-sulphamoylacetophenone 86 g (0.344 mol) of 2-methoxy-5-chlorosulphonylacetophenone and 690 ml of chloroform are introduced into a 1-liter round-bottomed flask. The mixture is stirred until dissolution has taken place and then cooled to 0° C. in an ice bath, and a stream of ammonia is passed into the solution for 1 hour. The mixture is thereafter allowed to return to room temperature, the solvent is then evaporated off and 250 ml of 1M hydrochloric acid are added. The suspension obtained is stirred for 3 hours, and the product is then filtered off, washed with ice-cold water and dried in a desiccator under vacuum over phosphorus pentoxide. 72.8 g of product are obtained.
Melting point: 161–162° C.

According to the same process, 2-methyl-5-sulphamoylacetophenone was obtained.
Melting point: 215° C.

2.3. α-Bromo-2-methoxy-5-sulphamoylacetophenone 60.36 g (0.262 mol) of 2-methoxy-5-sulphamoylacetophenone and 530 ml of acetic acid are introduced into a 1-liter three-necked flask. The mixture is stirred and heated to 50° C. 41.95 g (0.262 mol) of bromine are then added dropwise, and the mixture is stirred for 16 hours while it is allowed to return to room temperature, and is filtered. The precipitate is washed with a minimum amount of ethanol and dried in a desiccator under vacuum over phosphorus pentoxide. 49 g of product are obtained.
Melting point: 154–156° C.

2.4. α-Azido-2-methoxy-5-sulphamoylacetophenone 7 g (0.023 mol) of α-bromo-2-methoxy-5-sulphamoylacetophenone, 2.6 ml (0.045 mol) of acetic acid and 23 ml of ethanol are introduced into a 100-ml three-necked flask. The suspension is heated to 50° C. while being stirred, and a solution of 2.94 g (0.045 mol) of sodium azide in 8 ml of water is then added dropwise. The suspension is stirred at 50° C. for 45 minutes and then allowed to return to room temperature. The precipitate is filtered off, washed with a minimum amount of cold ethanol and then dried in a desiccator under vacuum over phosphorus pentoxide. 5.46 g of product are obtained.
Melting point: 155–160° C. (with decomposition).

2.5. (−)-α-Azidomethyl-2-methoxy-5-sulphamoylbenzenemethanol 16.2 g (0.060 mol) of α-azido-2-methoxy-5-sulphamoylacetophenone and 240 ml of anhydrous tetrahydrofuran are introduced into a 500-ml three-necked flask. The solution is cooled to −25° C., and a solution of 38.5 g (0.12 mol) of (−)-DIP-Cl in 30 ml of anhydrous tetrahydrofuran is added at a flow rate of 1.5 ml/min. After 90 minutes, the solution is allowed to return to room temperature and 10 ml of methanol are added. The reaction mixture is then concentrated and the residue is purified by column chromatography with a 40:60 mixture of petroleum ether and ethyl acetate. After recrystallization in isopropanol and drying in a desiccator under vacuum over phosphorus pentoxide, 11.55 g of product (ee=99.9%) are obtained.
Melting point: 122–125° C.
$[\alpha]_D^{20}$=−147.7° (c=1, dimethyl sulphoxide)

2.6. (−)-α-Aminomethyl-2-methoxy-5-sulphamoylbenzenemethanol 11 g (0.040 mol) of (−)-α-azidomethyl-2-methoxy-5-sulphamoylbenzenemethanol, 500 ml of ethanol and 2.2 g of 10% palladium on charcoal are introduced into a 1-liter reactor. The reactor is closed and purged with nitrogen, and the mixture is stirred under 400 kPa of hydrogen at room temperature for 3 hours. The reaction mixture is then filtered through Whatman paper, the recovered catalyst is suspended in 200 ml of methanol and the mixture is heated to boiling for 30 minutes. It is then filtered through Whatman paper, the filtrates are combined and concentrated and the residue is dried in a desiccator under vacuum over phosphorus pentoxide. 9.4 g of (−)-α-aminomethyl-2-methoxy-5-sulphamoylbenzenemethanol are obtained.

On recrystallization of the product in 388 ml of methanol, 5.46 g of product are obtained. Moreover, by concentration of the mother liquors and recrystallization of the residue in 400 ml of ethanol, 1.93 g of product are obtained, that is to say 7.39 g of product in total.
Melting point: 217–220° C.
$[\alpha]_D^{20}$=−85.2° (methanol)

2.7. (−)-α-Aminomethyl-2-methoxy-5-sulphamoylbenzenemethanol methanesulphonate 1 equivalent of methanesulphonic acid in 2M solution in methanol is added to the product obtained in the preceding step. After recrystallization in methanol and diethyl ether and drying of the product in a desiccator under vacuum over phosphorus pentoxide, (−)-α-aminomethyl-2-methoxy-5-sulphamoylbenzenemethanol methanesulphonate is obtained.
Melting point: 232–233° C.
$[\alpha]_D^{20}$=−41.0° (c=0.796, water)

EXAMPLE 3

(+)- and (−)-α-aminomethyl-2-methoxy-5-sulphamoylbenzenemethanol methanesulphonate 3.1. α-Chloro-2-methoxy-5-sulphamoylacetophenone 4.36 g (14.1 mmol) of α-bromo-2-methoxy-5-sulphamoylacetophenone, 200 ml of anhydrous acetone and 50 g of lithium chloride are introduced into a 500-ml round-bottomed flask. The mixture is heated to reflux for 16 hours, the solution is then concentrated, 200 ml of water are added and the mixture is extracted with 3 times 80 ml of ethyl acetate. The organic phases are combined, dried over magnesium sulphate and concentrated. 3.56 g of product are obtained.

Melting point: 162° C.

3.2. α-Chloromethyl-2-methoxy-5-sulphamoylbenzenemethanol 10 ml of anhydrous tetrahydrofuran and 4 ml of a 1M solution of borane in tetrahydrofuran are introduced into a 100-ml round-bottomed flask. A solution of 1.0 g (3.8 mmol) of α-chloro-2-methoxy-5-sulphamoylacetophenone in 10 ml of tetrahydrofuran is added dropwise. The mixture is stirred for 10 hours at room temperature and 10 ml of methanol are then added. The solution is concentrated, 40 ml of water are added and the mixture is extracted with 3 times 60 ml of ethyl acetate. The organic phases are combined, dried over magnesium sulphate and concentrated. 1.0 g of product is obtained.

Melting point: 112° C.

3.3. (+)-α-Chloromethyl-2-methoxy-5-sulphamoylbenzyl acetate 2.64 g (9.9 mmol) of α-chloromethyl-2-methoxy-5-sulphamoylbenzenemethanol and 100 ml of dichloromethane are introduced into a 250-ml round-bottomed flask. 10 ml of dimethylformamide are then added with stirring, followed by 852 μl of acetic acid, 2.56 g of dicyclohexylcarbodiimide and 121 mg of dimethylaminopyridine. The mixture is allowed to react for 1 hour at room temperature, and is then filtered and rinsed with 50 ml of 5% sodium hydrogen carbonate solution and then with 50 ml of water. The rinsing liquors are extracted with 2 times 20 ml of acetic acid, and the organic phases are then combined, dried and concentrated. On chromatographing the residue on a silica column with a 25:75 mixture of ethyl acetate and cyclohexane, 1.9 g of product are obtained.

Melting point: 131° C.

3.4. (+)- and (−)-α-chloromethyl-2-methoxy-5-sulphamoylbenzenemethanol 2.86 g (9.3 mmol) of (±)-α-chloromethyl-2-methoxy-5-sulphamoylbenzyl acetate and 110 ml of t-butyl methyl ether are introduced into a 500-ml three-necked flask. The mixture is stirred for 15 minutes, 170 ml of phosphate buffer are then added and the mixture is stirred vigorously until an emulsion is obtained. 0.57 g (20%) of lipase SP 523 is then added and the reaction is monitored at room temperature using a pH-stat (addition of 1M sodium hydroxide) and by HPLC on a chiral column, and the degree of conversion of the ester and the enantiomeric excesses of the ester and of the alcohol are determined. After 45 hours of reaction, when the enantiomeric excesses of the ester and of the alcohol are greater than 95%, the reaction medium is diluted with 800 ml of ethyl acetate, the organic phase is separated and the aqueous phase is re-extracted with 3 times 500 ml of ethyl acetate. The organic phases are combined, dried and concentrated, and the residue is purified by 2 successive flash chromatographic runs on a silica column with a 30:70 mixture of ethyl acetate and cyclohexane. 1.32 g of (−)-α-chloromethyl-2-methoxy-5-sulphamoylbenzyl acetate (ee=99%) and 1.05 g of (+)-α-chloromethyl-2-methoxy-5-sulphamoylbenzenemethanol are obtained.

The (+) enantiomer is purified by dissolution in 10 ml of ethyl acetate and recrystallization on adding hexane (ee=98%).

Melting point: 117–118° C.

$[\alpha]_D^{20}$=+40° (c=0.305, methanol)

61 μl of acetyl chloride are added to 100 ml of methanol and the mixture is stirred for 15 minutes. 1.32 g (−)-α-chloromethyl-2-methoxy-5-sulphamoylbenzyl acetate are then added and the mixture is heated to reflux for 1 hour (degree of conversion of 97% shown by HPLC). The mixture is thereafter evaporated, the residue is then taken up in 100 ml of ethyl acetate and the medium is neutralized with 5 ml of 2% ethyl hydrogen carbonate. The carbonate phase is extracted with 2 times 5 ml of ethyl acetate, the organic phases are then combined, dried and concentrated to 30 ml and cyclohexane is added. After one night at room temperature, the product which has crystallized is filtered off. 1 g of (−)-α-chloromethyl-2-methoxy-5-sulphamoylbenzenemethanol is obtained.

Melting point: 114–115° C.

$[\alpha]_D^{20}$=−41.4° (c=0.295, methanol)

3.5. (+)-α-Azidomethyl-2-methoxy-5-sulphamoylbenzenemethanol 1.58 g (5.9 mmol) of (+)-α-chloromethyl-2-methoxy-5-sulphamoylbenzenemethanol, 20 ml of dimethylformamide and 1.54 g of sodium azide are introduced into a 250-ml round-bottomed flask. The reaction mixture is heated to 110° C. for 16 hours, 200 ml of water are then added and the mixture is extracted with 3 times 80 ml of ethyl acetate. The organic phases are then combined, dried over magnesium sulphate and concentrated. 1.2 g of product are obtained.

Melting point: 122° C.

$[\alpha]_D^{20}$=+144° (c=1, dimethyl sulphoxide)

According to the same process, starting from (−)-α-chloromethyl-2-methoxy-5-sulphamoylbenzenemethanol, (−)-α-azidomethyl-2-methoxy-5-sulphamoylbenzenemethanol was obtained.

Melting point: 122° C.

$[\alpha]_D^{20}$=147.7° (c=1, dimethyl sulphoxide)

3.6. (+)-α-Aminomethyl-2-methoxy-5-sulphamoylbenzenemethanol

Starting from (+)-α-azidomethyl-2-methoxy-5-sulphamoylbenzenemethanol treated under the conditions described in step 6 of Example 2, (+)-α-aminomethyl-2-methoxy-5-sulphamoylbenzenemethanol was obtained.

Melting point: 217–220° C.

$[\alpha]_D^{20}$=+40° (c=1, dimethyl sulphoxide)

According to the same process, starting from (−)-α-azidomethyl-2-methoxy-5-sulphamoylbenzenemethanol, (−)-α-aminomethyl-2-methoxy-5-sulphamoylbenzenemethanol was obtained.

Melting point: 217–220° C.

$[\alpha]_D^{20}$=−44° (c=1, dimethyl sulphoxide)

3.7. (+)-α-Aminomethyl-2-methoxy-5-sulphamoylbenzenemethanol methanesulphonate

Starting from (+)-α-aminomethyl-2-methoxy-5-sulphamoylbenzenemethanol treated with 1 equivalent of methanesulphonic acid in 2M solution in methanol, recrystallization in methanol and diethyl ether and drying in a desiccator under vacuum over phosphorus pentoxide, (+)-α-aminomethyl-2-methoxy-5-sulphamoylbenzenemethanol methanesulphonate was obtained.

Melting point: 234° C.

$[\alpha]_D^{20}$=+41° (c=0.9945, water)

According to the same process, starting from (−)-α-aminomethyl-2-methoxy-5-sulphamoylbenzenemethanol, (−)-α-aminomethyl-2-methoxy-5-sulphamoylbenzenemethanol methanesulphonate was obtained.

Melting point: 235° C.

$[\alpha]_D^{20}$=−37.3° (c=0.969, methanol/water 80:20)

EXAMPLE 4

(+) and (−)-α-aminomethyl-2-methoxy-5-sulphamoylbenzenemethanol methanesulphonate 4.1. (±)-α-Azidomethyl-2-methoxy-5-sulphamoylbenzenemethanol 5 g (18.5 mmol) of α-azido-2-methoxy-5-sulphamoylacetophenone and 150 ml of methanol are introduced into a 500-ml round-bottomed flask. The solution is cooled to 0° C. and 0.963 g (16.6 mmol) of sodium borohydride is then added. The solution is stirred for 10 minutes and then allowed to return to room temperature, and 15 ml of 5% hydrochloric acid solution are added. The reaction mixture is thereafter concentrated, and the residue is then purified by column chromatography with a 40:60 mixture of petroleum ether and ethyl acetate and dried in a desiccator under vacuum over phosphorus pentoxide.

3.85 g of product are obtained.

Melting point: 123° C.

4.2. (+)- and (−)-α-azidomethyl-2-methoxy-5-sulphamoylbenzenemethanol N-carbobenzyloxy-L-alanine ester 4.66 g (20.9 mmol) of N-carbobenzyloxy-L-alanine, 25 ml of dichloromethane and 3.58 g (17.4 mmol) of 1,3-dicyclohexylcarbodiimide are introduced into a 250-ml round-bottomed flask. The mixture is stirred for 20 minutes at room temperature, and 3.8 g (13.9 mmol) of α-azidomethyl-2-methoxy-5-sulphamoylbenzenemethanol and 0.17 g (0.14 mmol) of dimethylaminopyridine are then added. The reaction medium is stirred for 2 hours and then concentrated under vacuum, and the residue is purified by several chromatographic runs on a silica column with a 99:1 mixture of dichloromethane and acetone. 1.58 g of (+)-α-azidomethyl-2-methoxy-5-sulphamoylbenzenemethanol N-carbobenzyloxy-L-alanine ester and 2.92 g of (−)-α-azidomethyl-2-methoxy-5-sulphamoylbenzenemethanol N-carbobenzyloxy-L-alanine ester are obtained.

Melting point: 170° C. (with decomposition)

4.3. (+)-Azidomethyl-2-methoxy-5-sulphamoylbenzenemethanol 0.91 g (1.9 mmol) of (+)-α-azidomethyl-2-methoxy-5-sulphamoylbenzenemethanol N-carbobenzyloxy-L-alanine ester, 20 ml of ethanol and 3 ml of a 1M solution of potassium hydroxide in a 1:1 mixture of ethanol and water are introduced into a 100-ml round-bottomed flask. The reaction mixture is stirred for 25 minutes at room temperature and then concentrated under vacuum, and the residue is purified by column chromatography with a 95:5 mixture of dichloromethane and methanol.

0.41 g of product is obtained.

Melting point: 122° C.

According to the same process, starting from (−)-α-azidomethyl-2-methoxy-5-sulphamoylbenzenemethanol N-carbobenzyloxy-L-alanine ester, (−)-α-azidomethyl-2-methoxy-5-sulphamoylbenzenemethanol was obtained.

Melting point: 122° C.

4.4. (+)-α-Aminomethyl-2-methoxy-5-sulphamoylbenzenemethanol methanesulphonate

Starting from (+)-α-azidomethyl-2-methoxy-5-sulphamoylbenzenemethanol, hydrogenated under the conditions described in step 6 of Example 2 and then treated with 1 equivalent of methanesulphonic acid, (+)-α-aminomethyl-2-methoxy-5-sulphamoylbenzenemethanol methanesulphonate was obtained.

Melting point: 235° C.

$[\alpha]_D^{20} = +35°$ (c=1, methanol/water 80:20)

According to the same process, starting from (−)-α-azidomethyl-2-methoxy-5-sulphamoylbenzenemethanol, (−)-α-aminomethyl-2-methoxy-5-sulphamoylbenzenemethanol methanesulphonate was obtained.

Melting point: 233° C.

$[\alpha]_D^{20} = -41.8°$ (c=1, methanol/water 80:20)

EXAMPLE 5

α-diethylaminomethyl-2-methoxy-5-sulphamoylbenzenemethanol methanesulphonate 5.1. 2-Methoxy-5-sulphamoylstyrene oxide 2 g (6.5 mmol) of α-bromo-2-methoxy-5-sulphamoylacetophenone, 20 ml of anhydrous ethanol and 1.0 g (7.0 mmol) of potassium carbonate are introduced into 100-ml round-bottomed flask. 0.41 g (10.8 mmol) of sodium borohydride is then added, the mixture is stirred at room temperature for 20 minutes, 0.1M of sodium hydroxide is added thereafter and the mixture is stirred for 30 minutes. The solution is concentrated, 30 ml of water are added and the mixture is extracted with 3 times 30 ml of ethyl acetate. The organic phases are combined, dried over magnesium sulphate and concentrated. 1.41 g of product are obtained.

Melting point: 118° C.

5.2. α-Diethylaminomethyl-2-methoxy-5-sulphamoylbenzenemethanol methanesulphonate 1.41 g (6.1 mmol) of 2-methoxy-5-sulphamoylstyrene oxide, 10 ml of anhydrous ethanol and 17.8 g (244 mmol) of diethylamine are introduced into a 100-ml round-bottomed flask. The mixture is heated to reflux with stirring for 16 hours and the solution is then concentrated. The residue is purified by column chromatography with a 90:9:1 mixture of dichloromethane, methanol and aqueous ammonia, and then dried in a desiccator under vacuum over phosphorus pentoxide. 1.42 g of product are obtained in the form of an oil, which is treated with 1 equivalent of methanesulphonic acid in 2M solution in methanol. After recrystallization in methanol and diethyl ether and drying in a desiccator under vacuum over phosphorus pentoxide, 0.875 g of α-diethylaminomethyl-2-methoxy-5-sulphamoylbenzenemethanol methanesulphonate is obtained.

Melting point: 90–92° C.

EXAMPLE 6

α-methylaminomethyl-2-methoxy-5-sulphamoylbenzenemethanol methanesulphonate 6.1. α-Benzylmethylaminomethyl-2-methoxy-5-sulphamoylbenzenemethanol 2-Methoxy-5-sulphamoylstyrene oxide obtained in step 1 of Example 5, treated with benzylmethylamine under the conditions described in step 2 of Example 5, gives α-benzylmethylaminomethyl-2-methoxy-5-sulphamoylbenzenemethanol in the form of an oil.

6.2. α-Methylaminomethyl-2-methoxy-5-sulphamoylbenzenemethanol methanesulphonate On hydrogenation of 1.90 g (5.4 mmol) of α-benzylmethylaminomethyl-2-methoxy-5-sulphamoylbenzenemethanol under the conditions described in step 6 of Example 2, α-methylaminomethyl-2-methoxy-5-sulphamoylbenzenemethanol is obtained. After recrystallization in ethyl acetate and methanol, the product obtained is treated with 1 equivalent of methanesulphonic acid in 2M solution in methanol, and the salt is recrystallized from methanol, dichloromethane and diethyl ether. 0.396 g of α-methylaminomethyl-2-methoxy-5-sulphamoylbenzenemethanol methanesulphonate is thereby obtained.

Melting point: 194–196° C.

EXAMPLE 7

α-aminomethyl-2-fluoro-5-sulphamoylbenzenemethanol methanesulphonate 7.1. 2-Fluoro-5-nitroacetophenone 25 ml (180 mmol) of 2-fluoroacetophenone are introduced dropwise into a 100-ml three-necked flask containing 60 ml of concentrated sulphuric acid cooled to −5° C. A mixture of 14 ml of nitric acid (d=1.42) and 20 ml of concentrated sulphuric acid is then added dropwise without exceeding 0° C. The mixture is stirred at −5° C. for 30 minutes and then poured onto crushed ice. The resulting mixture is thereafter extracted with 3 times 60 ml of ethyl acetate, and the organic phases are then combined, dried over magnesium sulphate and concentrated. The residue is purified by column chromatography with a 70:30 mixture of hexane and ethyl acetate, and then dried in a desiccator under vacuum over phosphorus pentoxide. 26 g of product are obtained.
Melting point: 72° C.

According to the same process, the following compounds were obtained:
2-chloro-5-nitroacetophenone.
Melting point: 65° C.
2-hydroxy-5-nitroacetophenone.
Melting point: 98° C.,
which is converted by a phase transfer catalysis reaction with isopropyl iodide to 2-isopropoxy-5-nitroacetophenone,
Melting point: 78° C.

7.2. 5-Amino-2-fluoroacetophenone 25.4 g (152 mmol) of 2-fluoro-5-nitroacetophenone, 343 g (1.52 mol) of tin chloride dihydrate and 250 ml of ethyl acetate are introduced into a 1-liter three-necked flask. The reaction mixture is heated to 70° C. for 30 minutes and then poured onto 1 liter of crushed ice, 30% sodium hydroxide solution is added and the mixture is extracted with 3 times 350 ml of ethyl acetate. The organic phases are combined, dried over magnesium sulphate and concentrated. 11.26 g of product are obtained in the form of an oil.

According to the same process, the following compounds were obtained:
5-amino-2-chloroacetophenone, in the form of an oil.
5-amino-2-isopropoxyacetophenone, in the form of an oil.

7.3. 2-Fluoro-5-sulphamoylacetophenone 15.3 g (100 mmol) of 5-amino-2-fluoroacetophenone and 50 ml of acetic acid are introduced into a 250-ml three-necked flask, and 50 ml of concentrated hydrochloric acid are then added. The reaction mixture is cooled to 0° C., a solution of 10.3 g (150 mmol) of sodium nitrite in 25 ml of water is then added dropwise and the mixture is left at 0C for 30 minutes. A suspension, cooled to −15° C., of 5 g (29 mmol) of cuprous chloride dihydrate and 30 g (470 mmol) of sulphur dioxide in 75 ml of acetic acid is then added. The mixture is maintained at 0° C. for 48 hours, 20 ml of water are then added, the resulting mixture is extracted with 3 times 120 ml of dichloromethane, and the organic phases are then combined, dried over magnesium sulphate and concentrated.

The residue is dissolved in 100 ml of tetrahydrofuran, and 28% aqueous ammonia solution is then added dropwise at 0° C. The reaction mixture is stirred for 16 hours at room temperature and then concentrated. The residue is purified by column chromatography with a 60:40 mixture of hexane and ethyl acetate and dried in a desiccator under vacuum over phosphorus pentoxide. 11.23 g of product are obtained.
Melting point: 112° C.

According to the same process, the following compounds were obtained:
2-chloro-5-sulphamoylacetophenone.
Melting point: 106° C.
2-isopropoxy-5-sulphamoylacetophenone.
Melting point: 85° C.
3-sulphamoylacetophenone.
Melting point: 144° C.

7.4. α-Bromo-2-fluoro-5-sulphamoylacetophenone

Starting from 2-fluoro-5-sulphamoyl-acetophenone, treated under the conditions described in step 3 of Example 2, α-bromo-2-fluoro-5-sulphamoylacetophenone was obtained.
Melting point: 122° C.

According to the same process, the following compounds were obtained:
α-bromo-2-chloro—S—sulphamoylacetophenone.
Melting point: 126° C.
α-bromo-2-isopropoxy-5-sulphamoylacetophenone.
Melting point: 105° C.
α-bromo-3-sulphamoylacetophenone
Melting point: 130° C.

7.5. α-Chloro-2-fluoro-5-sulphamoylacetophenone

Starting from α-bromo-2-fluoro-5-sulphamoylacetophenone, treated under the conditions described in step 1 of Example 3, α-chloro-2-fluoro-5-sulphamoylacetophenone was obtained.
Melting point: 114° C.

According to the same process, the following compounds were obtained:
α-chloro-2-chloro-5-sulphamoylacetophenone
Melting point: 124° C.
α-chloro-2-isopropoxy-5-sulphamoylacetophenone
Melting point: 98° C.
α-chloro-3-sulphamoylacetophenone.
Melting point: 128° C.

7.6. α-Chloromethyl-2-fluoro-5-sulphamoylbenzenemethanol

Starting from α-chloro-2-fluoro-5-sulphamoylacetophenone, treated under the conditions of step 2 of Example 3, α-chloromethyl-2-fluoro-5-sulphamoylbenzenemethanol was obtained.
Melting point: 112° C.

According to the same process, the following compounds were obtained:
α-chloromethyl-2-chloro-5-sulphamoylbenzenemethanol.
Melting point: 115° C.
α-chloromethyl-2-isopropoxy-5-sulphamoylbenzenemethanol.
Melting point: 93° C.
α-chloromethyl-3-sulphamoylbenzenemethanol.
Melting point: 122° C.

7.7. α-Azidomethyl-2-fluoro-5-sulphamoylbenzenemethanol

Starting from α-chloromethyl-2-fluoro-5-sulphamoylbenzenemethanol, treated under the conditions described in step 4 of Example 3, α-azidomethyl-2-fluoro-5-sulphamoylbenzenemethanol was obtained.
Melting point: 86° C.

According to the same process, the following compounds were obtained:
α-azidomethyl-2-chloro-5-sulphamoylbenzenemethanol.
Melting point: 122° C.
α-azidomethyl-2-isopropoxy-5-sulphamoylbenzenemethanol.
Melting point: 95° C.
α-azidomethyl-3-sulphamoylbenzenemethanol.
Melting point: 118° C.

7.8. α-Aminomethyl-2-fluoro-5-sulphamoylbenzenemethanol methanesulphonate

Starting from α-azidomethyl-2-fluoro-5-sulphamoylbenzenemethanol, treated under the conditions of step 6 of Example 2, α-aminomethyl-2-fluoro-5-sulphamoylbenzenemethanol methanesulphonate was obtained.
Melting point: 164° C.

EXAMPLE 8

α-aminomethyl-2-methyl-5-sulphamoylbenzenemethanol methanesulphonate 8.1. α-Chloro-2-methyl-5-sulphamoylacetophenone 26.4 g (76.0 mmol) of benzyltrimethylammonium dichloroiodate (prepared according to the method described in Synthesis 7, (1988), 545), 9.25 g (43.4 mmol) of 2-methyl-5-sulphamoylacetophenone, 90 ml of methanol and 220 ml of 1,2-dichloroethane are introduced into a 500-ml round-bottomed flask. The reaction medium is heated to reflux for 16 hours and then concentrated, and 200 ml saturated sodium bicarbonate solution are added. The mixture is extracted with 3 times 120 ml of ethyl acetate, and the organic phases are then combined, dried over magnesium sulphate and concentrated. The residue is purified by column chromatography with a 60:40 mixture of hexane and ethyl acetate and dried in a desiccator under vacuum over phosphorus pentoxide. 1.7 g of product are obtained.

Melting point: 114° C.

8.2. α-Chloromethyl-2-methyl-5-sulphamoylbenzenemethanol

Starting from α-chloro-2-methyl-5-sulphamoylacetophenone, treated under the conditions of step 2 of Example 3, α-chloromethyl-2-methyl-5-sulphamoylbenzenemethanol was obtained.

Melting point: 126° C.

8.3. α-Azidomethyl-2-methyl-5-sulphamoylbenzenemethanol

Starting from α-chloromethyl-2-methyl-5-sulphamoylbenzenemethanol, treated under the conditions described in step 4 of Example 3, α-azidomethyl-2-methyl-5-sulphamoylbenzenemethanol was obtained.

Melting point: 98° C.

8.4. α-Aminomethyl-2-methyl-5-sulphamoylbenzenemethanol methanesulphonate

Starting from α-azidomethyl-2-methyl-5-sulphamoylbenzenemethanol, treated under the conditions described in step 6 of Example 6, α-aminomethyl-2-methyl-5-sulphamoylbenzenemethanol methanesulphonate was obtained.

Melting point: 185° C.

EXAMPLE 9

α-aminomethyl-2-chloro-5-sulphamoylbenzenemethanol methanesulphonate 1.35 g (4.9 mmol) of α-azidomethyl-2-chloro-5-sulphamoylbenzenemethanol, 90 ml of anhydrous pyridine and 9.67 g (29.0 mmol) of triphenylphosphine on a carrier are introduced into a 250-ml round-bottomed flask. The mixture is stirred at room temperature for 9 hours, 100 ml of 28% aqueous ammonia are then added, and the suspension is stirred for 16 hours and filtered. The filtrate is concentrated and the residue is recrystallized in methanol. 0.523 g of α-aminomethyl-2-chloro-5-sulphamoylbenzenemethanol is obtained. 1 equivalent of methanesulphonic acid in 2M solution in methanol is added. After recrystallization in methanol and diethyl ether and drying in a desiccator under vacuum over phosphorus pentoxide, 0.439 g of α-aminomethyl-2-chloro-5-sulphamoylbenzenemethanol methanesulphonate is obtained.

Melting point: 206–208° C.

EXAMPLE 10 syn- and anti-(2'-methoxy-5'-aminosulphonylphenyl)-2-amino-1-propanol 10.1. 2-Methoxy-5-chlorosulphonylpropiophenone Starting from 2-methoxypropiophenone, treated under the conditions of step 1 of Example 2, 2-methoxy-5-chlorosulphonylpropiophenone was obtained.

Melting point: 86–89° C.

10.2. 2-Methoxy-5-sulphamoylpropiophenone

Starting from 2-methoxy-5-chlorosulphonylpropiophenone, treated under the conditions of step 2 of Example 2, 2-methoxy-5-sulphamoylpropiophenone was obtained.

Melting point: 162–165° C.

10.3. 2-Bromo-2'-methoxy-5'-sulphamoylpropiophenone

Starting from 2-methoxy-5-sulphamoylpropiophenone, treated under the conditions of step 3 of Example 2, 2-bromo-2'-methoxy-5'-sulphamoylpropiophenone was obtained.

Melting point: 108–110° C.

10.4. 2-Azido-2'-methoxy-5'-sulphamoylpropiophenone

Starting from α-bromo-2-methoxy-5-sulphamoylpropiophenone, treated under the conditions of step 4 of Example 2, 2-azido-2'-methoxy-5'-sulphamoylpropiophenone was obtained.

Melting point: 113–114° C.

10.5. (2'-Methoxy-5'-aminosulphonylphenyl)-2-azido-1-propanol

Starting from 2-azido-2'-methoxy-5'-sulphamoylpropiophenone, treated under the conditions of step 1 of Example 4, (2'-methoxy-5'-aminosulphonylphenyl)-2-azido-1-propanol was obtained.

Melting point: 109–110° C.

10.6. Syn- and anti-(2'-methoxy-5'-aminosulphonylphenyl)-2-amino-1-propanol

Starting from (2'-methoxy-5'-aminosulphonylphenyl)-2-azido-1-propanol, treated under the conditions of step 6 of Example 2, a mixture of syn- and anti-(2'-methoxy-5'-aminosulphonylphenyl)-2-amino-1-propanol was obtained, which products are separated by successive chromatographic runs on a silica column with a 95:5:0.5 dichloromethane/methanol/ammonia elution solvent to yield the syn and anti diastereoisomers.

After recrystallization in isopropanol and drying in a desiccator under vacuum over phosphorus pentoxide, syn-(2'-methoxy-5'-aminosulphonylphenyl)-2-amino-1-propanol was obtained.

Melting point: 176–177° C., and anti-(2'-methoxy-5'-aminosulphonylphenyl)-2-amino-1-propanol was obtained.

Melting point: 233–237° C.

EXAMPLE 11

(−)-syn-(2'-methoxy-5'-sulphamoylphenyl)-2-amino-1-propanol 11.1. (−)-Syn-(2'-methoxy-5'-sulphamoylphenyl)-2-azido-1-propanol Starting from 2-azido-2'-methoxy-5'-sulphamoylpropiophenone, treated under the conditions of step 5 of Example 2, (−)-syn-(2'-methoxy-5'-sulphamoylphenyl)-2-amino-1-propanol was obtained after 2 recrystallizations in isopropanol.

Melting point: 143–145° C.

$[\alpha]_D^{20}$=−125° (methanol)

11.2. (−)-Syn-(2'-methoxy-5'-sulphamoylphenyl)-2-amino-1-propanol

Starting from (−)-syn-(2'-methoxy-5'-aminosulphonylphenyl)-2-azido-1-propanol, treated under the conditions of step 6 of Example 2, (−)-syn-(2'-methoxy-5'-sulphamoylphenyl)-2-amino-1-propanol was obtained after 2 recrystallizations in isopropanol.

Melting point: 190–191° C.

$[\alpha]_D^{20}$=−34.1° (methanol)

The compounds of the invention are collated in the table which follows, with their physical properties.

TABLE

Formula (I): phenyl ring with R1 at ortho position, SO2NHR4 at meta/para, side chain -CH(OH)-CH(R5)-N(R2)(R3)

| No. | R₁ | R₂ | R₃ | R₄ | R₅ | base/salt | M.p. (° C.) |
|---|---|---|---|---|---|---|---|
| 1 | H | H | H | H | H | MeSO3H | 156–161 |
| 2 | Me | H | H | H | H | MeSO3H | 185 |
| 3 (±) | OMe | H | H | H | H | base | 217–220 |
|  |  |  |  |  |  | MeSO3H | 210–212 |
| 4 (+) | OMe | H | H | H | H | base | 217–220 |
|  |  |  |  |  |  | MeSO3H | 234 |
| 5 (−) | OMe | H | H | H | H | base | 217–220 |
|  |  |  |  |  |  | MeSO3H | 235 |
| 6 | O-iPr | H | H | H | H | MeSO3H | 92 |
| 7 | Cl | H | H | H | H | MeSO3H | 206–208 |
| 8 | F | H | H | H | H | MeSO3H | 164 |
| 9 | OMe | Me | H | H | H | MeSO3H | 194–196 |
| 10 | OMe | cyclopropyl | H | H | H | MeSO3H | 231 |
| 11 | OMe | Et | Et | H | H | MeSO3H | 90–92 |
| 12 | OMe | H | H | Me | H | oxalate | 154–156 |
| 13 | OMe | H | H | cyclopropyl | H | oxalate | 199–202 |
| 14 | OMe | H | H | i-Pr | H | oxalate | 180 |
| 15 | OMe | H | H | t-Bu | H | oxalate | 203–205 |
| 16 anti | OMe | H | H | H | CH₃ | Base | 233–237 |
| 17 syn | OMe | H | H | H | CH₃ | base | 176–177 |
| 18 (−) syn | OMe | H | H | H | CH₃ | base | 143–145 |

MeSO3H represents methanesulphonate
OMe represents methoxy
O-iPr represents isopropoxy
i-Pr represents isopropyl

represents cyclopropyl

The compounds of the invention were subjected to biological tests intended to demonstrate their $\alpha_1$-adrenoceptor agonist activity.

They were, in particular, subjected to tests of binding to the $\alpha_{1a}$, $\alpha_{1b}$ and $\alpha_{1d}$ sub-receptors, carried out, respectively, on rat salivary gland tissue, on rat liver tissue and on transfected CHO cells.

The affinity for each type of sub-receptor, expressed as the IC$_{50}$ (concentration inhibiting by 50% the binding to [$^3$H] prazosin), was determined, and the relative values of the affinity for the $\alpha_{1a}$ receptor with respect to the affinities for the $\alpha_{1b}$ and $\alpha_{1d}$ receptors, expressed as the ratios of the IC$_{50}$ values, [$\alpha_{1b}/\alpha_{1a}$] and [$\alpha_{1d}/\alpha_{1a}$], were calculated.

For the compounds of the invention, these ratios vary from 9.3 to 21.6 and from 7.8 to 20.9, respectively, indicating a substantial selectivity for the $\alpha_{1a}$ receptor.

The in vitro activity of the compounds of the invention was studied on urethral and arterial smooth muscles.

These experiments were carried out on female New Zealand rabbits weighing from 3 to 3.5 kg. The animals were killed by vertebral dislocation, and rings of tissue were then removed from mesenteric arteries and from the urethra. These rings of tissue were immersed in a modified Krebs solution and oxygenated with a mixture of 95% $O_2$ and 5% $CO_2$. Each sample of tissue was subjected to a tension of 1 g, phenylephrine was then introduced at cumulative doses and the dose/response curve was established. After rinsing of the samples, the test compound was introduced at cumulative doses and the dose/response curve was established. The $\alpha_1$-adrenergic effect of each compound is evaluated by calculating the pD$_2$ (negative logarithm of the concentration of antagonist in the presence of which the effect of a dose of the agonist is divided by 2), as well as by the maximum effect representing the percentage of the maximum contraction obtained with phenylephrine (% $E_{max}$)

For the compounds of the invention, the urethral and arterial pD$_2$ values vary between 4.18 and 4.93 (pD$_2$ phenylephrine=5.2–5.5) and between 3.73 and 4.55 (pD$_2$ phenylephrine=5.2–5.5), respectively, and the urethral and arterial % $E_{max}$ values vary between 58.4 and 76 and between 76 and 94.6, respectively.

The in vivo activity of the compounds of the invention on blood and urethral pressure was studied in rabbits.

These experiments were carried out on female New Zealand rabbits weighing from 3 to 4 kg. After pentobarbital anaesthesia, catheters were introduced into the abdominal aorta via the femoral artery, into a jugular vein and into the urethra (1 cm below the bladder neck).

The test compounds were administered 5 to 15 days after the operation, either intravenously or orally.

Intravenously, the compounds were administered over 5 minutes in a single dose, or in cumulative mode at intervals of 15 minutes between each dose, at doses of 3 to 100 µg/kg.

Blood pressure (BP) and urethral pressure (UP) were measured continuously for each dose.

For the compounds of the invention, the increase in BP is approximately 5 mmHg at a dose of 10 µg/kg and 15 mmHg at a dose of 100 µg/kg, and the increase in UP is approximately 14 cmH$_2$O at a dose of 10 µg/kg and 54 cmH$_2$O at a dose of 100 µg/kg.

At the different doses tested, the compounds of the invention display a strong uroselectivity, since they increase urethral pressure very substantially without significantly modifying blood pressure.

Orally, the compounds were administered by gavage in a single dose of 300 and 1000 µg/kg, in a volume of 1 ml/kg. The BP and UP were measured 5, 10, 30, 45 and 60 minutes after gavage.

For the compounds of the invention, the changes in BP are approximately −0.2 and −0.9 mmHg at the doses of 300 and 1000 µg/kg, respectively, after 30 minutes, and approximately −5.3 and 1.1 mmHg, respectively, after 60 minutes, and the changes in UP are approximately 1.6 and 7.8 cmH$_2$O at the doses of 300 and 1000 µg/kg, respectively, after 30 minutes, and approximately 3.7 and 8.3 cmH$_2$O respectively, after 60 minutes.

Orally, the compounds of the invention display complete uroselectivity, since urethral pressure is increased significantly without blood pressure being modified.

The results obtained collectively show that the compounds of the invention have a strong urethral action and a weak arterial action. They are $\alpha_1$-adrenoceptor agonists, selective for $\alpha_{1a}$ receptors. They may hence be used in the treatment of urinary incontinence.

For this purpose, they may be presented in all forms suitable for enteral or parenteral administration, in combination with pharmaceutical excipients, for example in the form of tablets, dragees, capsules including hard gelatin capsules, solutions to be taken orally or to be injected and suppositories, dosed so as to permit a daily dose of 0.001 to 1000 mg of active substance.

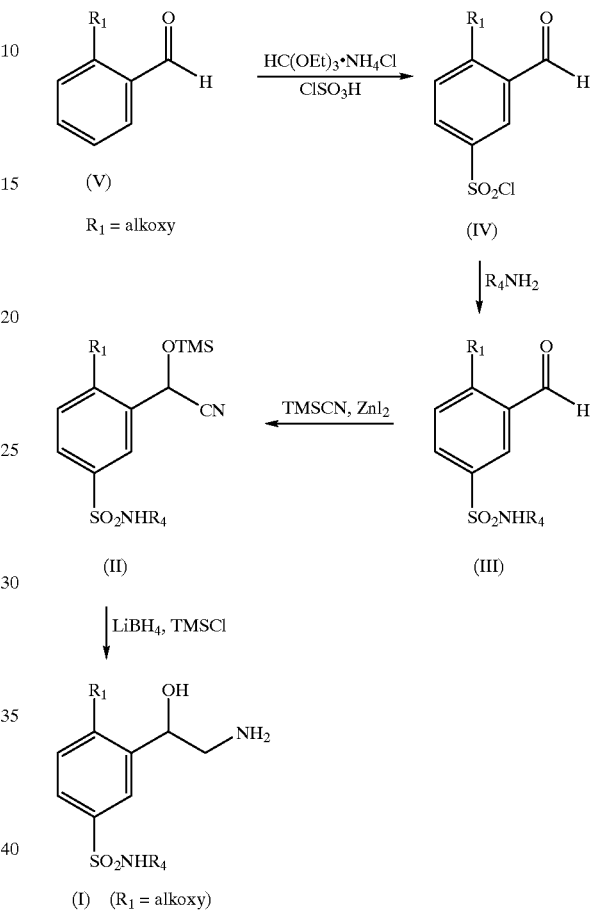

Appendix 1

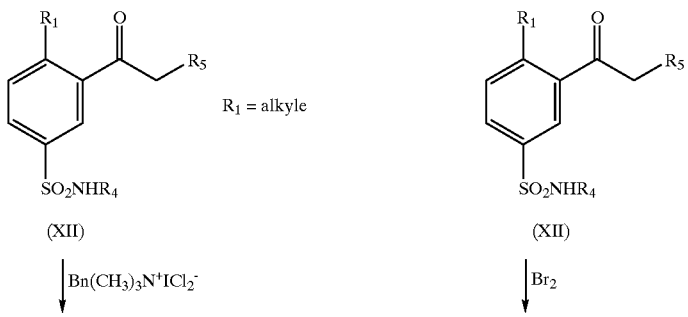

Appendix 2

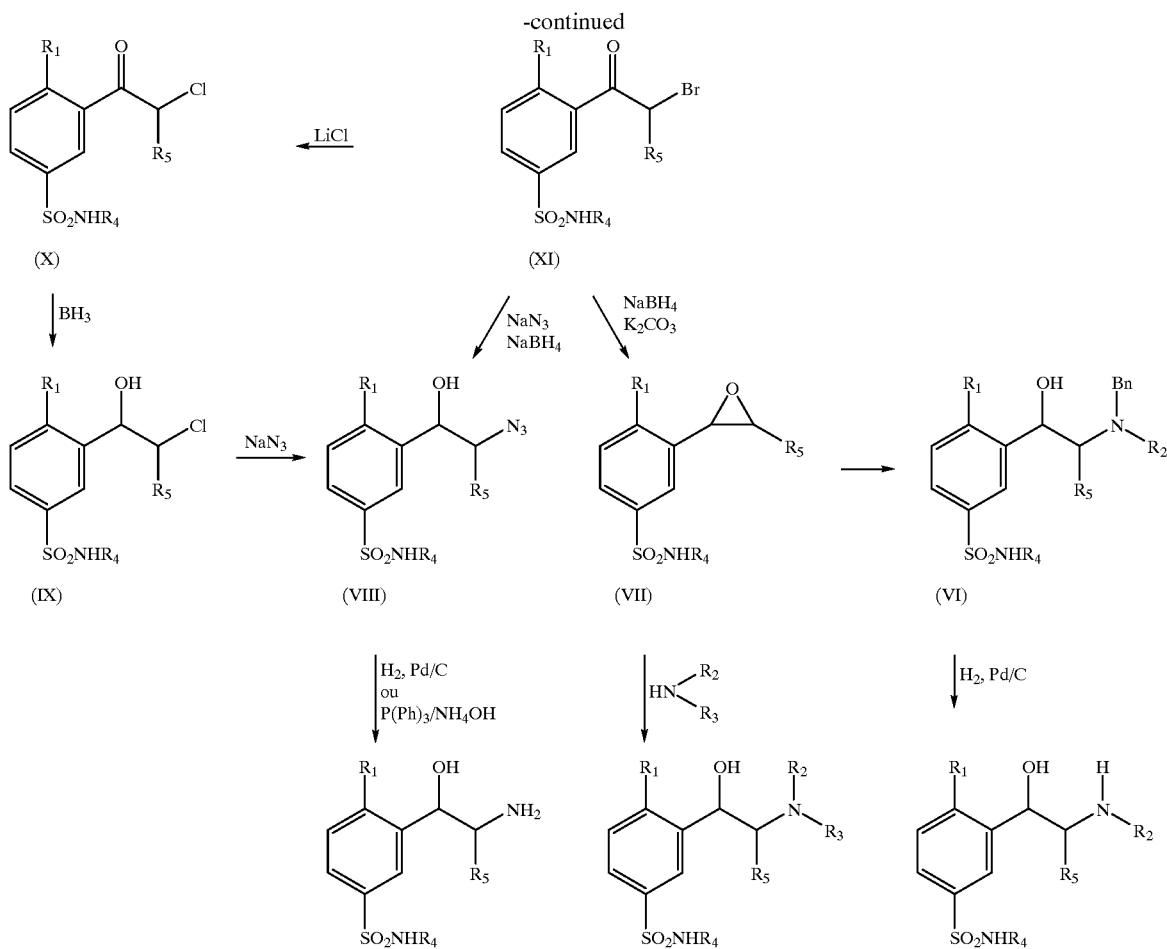

What is claimed is:

1. A benzenesulphonamide compound of formula (I):

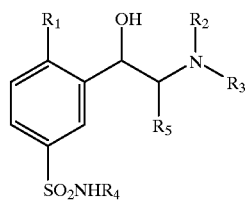

in which:
- $R_1$ represents a hydrogen atom, a halogen atom or a linear or branched $C_{1-4}$ alkyl or $C_{1-4}$ alkoxy group,
- $R_2$, $R_3$ and $R_4$ represent, independently of one another, a hydrogen atom or a linear, branched or cyclic $C_{1-4}$ alkyl group, and
- $R_5$ represents a hydrogen atom or a $C_{1-2}$ alkyl group, or an addition salt with a pharmaceutically acceptable acid thereof.

2. The compound according to claim 1, wherein $R_5$ represents a hydrogen atom or a methyl group.

3. The compound according to claim 1, wherein $R_1$ represents a hydrogen atom, a fluorine atom, a chlorine atom or a $C_{1-4}$ alkoxy group.

4. The compound according to claim 1, wherein $R_2$ and $R_3$ represent, independently of one another, a hydrogen atom, a methyl group, an ethyl group or an isopropyl group.

5. The compound according to claim 1, wherein $R_1$ represents a hydrogen atom, a fluorine atom, a chlorine atom or a $C_{1-4}$ alkoxy group,
- $R_2$ and $R_3$ represent, independently of one another, a hydrogen atom, a methyl group, an ethyl group or an isopropyl group,
- $R_4$ represents a hydrogen atom or a linear, branched or cyclic $C_{1-4}$ alkyl group, and
- $R_5$ represents a hydrogen atom, a methyl group or an ethyl group.

6. The compound according to claim 1, wherein $R_1$ represents a hydrogen atom, a fluorine atom, a chlorine atom, a methoxy group or an ethoxy group,
- $R_2$ and $R_3$ represent a hydrogen atom,
- $R_4$ represents a hydrogen atom or a linear, branched or cyclic $C_{1-4}$ alkyl group, and
- $R_5$ represents a hydrogen atom or a methyl group.

7. α-(Aminomethyl)-2-methoxy-5-sulphamoyl-benzenemethanol, its pharmaceutically acceptable acid addition salts and their enantiomers.

8. (+)-α-(Aminomethyl)-2-methoxy-5-sulpha-moylbenzenemethanol and its pharmaceutically acceptable acid addition salts.

9. (−)-α-(Aminomethyl)-2-methoxy-5-sulpha-moylbenzenemethanol and its pharmaceutically acceptable acid addition salts.

10. α-(Aminomethyl)-2-chloro-5-sulphamoyl-benzenemethanol, its pharmaceutically acceptable acid addition salts and their enantiomers.

11. α-(Aminomethyl)-2-fluoro-5-sulphamolyl-benzenemethanol, its pharmaceutically acceptable acid addition salts and their enantiomers.

12. A medicinal product, comprising a compound of formula (I) according to claim 1.

13. A pharmaceutical composition, comprising a compound of formula (I) according to claim 1 in combination with an excipient.

14. A process for preparing a compound of formula (I):

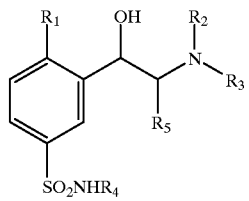

(I)

in which $R_1$ represents a linear or branched $C_{1-4}$ alkoxy group, and $R_2$ and $R_3$ represent a hydrogen atom, $R_4$ represents a hydrogen atom or a linear, branched or cyclic $C_{1-4}$ alkyl group, and $R_5$ represents a hydrogen atom, or an addition salt with a pharmaceutically acceptable acid thereof, which comprises:

(a) reacting a compound of formula (III):

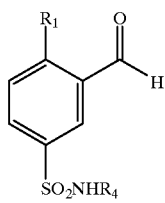

(III)

in which $R_1$ and $R_4$ are as defined above, with a trimethylsilyl cyanide in the presence of zinc iodide, to give the compound of formula (II):

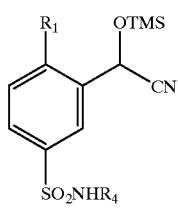

(II)

in which $R_1$ and $R_4$ are as defined above, (b) reducing the resulting compound of formula (II) with lithium borohydride in the presence of trimethylsilyl chloride, to give the resulting compound of formula (I), and (c) optionally converting the resulting compound (I) to its pharmaceutically acceptable acid addition salts.

15. A process for preparing a compound of formula (I):

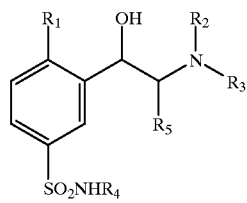

(I)

in which:

$R_1$ represents a hydrogen atom, a halogen atom or a linear or branched $C_{1-4}$ alkyl or $C_{1-4}$ alkoxy group, $R_2$, $R_3$ and $R_4$ represent, independently of one another, a hydrogen atom or a linear, branched or cyclic $C_{1-4}$ alkyl group, and $R_5$ represents a hydrogen atom or a $C_{1-2}$ alkyl group, or an addition salt with a pharmaceutically acceptable acid thereof, which comprises:

(a) either reacting a compound of formula (VIII):

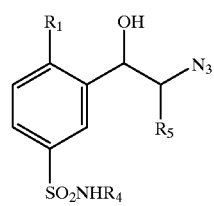

(VIII)

in which $R_4$ and $R_5$ are as defined above, either with hydrogen in the presence of a catalyst in the case where $R_1$ is defined as above with the exception of chlorine, or with triphenylphosphine and then aqueous ammonia in the case where $R_1$ is a chlorine atom, to prepare a compound of formula (I) in which $R_1$, $R_4$ and $R_5$ are as defined above and $R_2$ and $R_3$ are hydrogen atoms, (b) or reacting a compound of formula (VII):

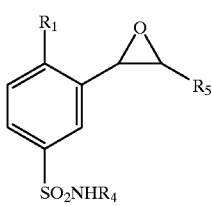

(VII)

in which $R_1$, $R_4$ and $R_5$ are as defined above, with an amine of formula $R_2(R_3)NH$ in which $R_2$ represents a hydrogen atom or a $C_{1-4}$ alkyl group and $R_3$ represents a $C_{1-4}$ alkyl group, to obtain a compound of formula (I) in which $R_2$ and $R_3$ are as defined above, or with an amine of formula $R_2(Bn)H$ in which $R_2$ is an alkyl group and Bn a benzyl group, to obtain a compound of formula (VI):

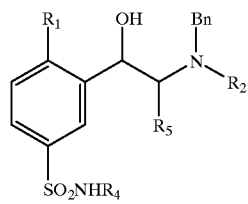
(VI)
in which $R_1$, $R_2$, $R_4$, $R_5$ and Bn are as defined above, reducing the compound of formula VI with hydrogen in the presence of a catalyst, to give a compound of formula (I) in which $R_2$ is a $C_{1-4}$ alkyl group, and
(c) optionally converting the resulting compound (I) to its pharmaceutically acceptable acid addition salts.
* * * * *